United States Patent
Tyagi et al.

(10) Patent No.: US 10,646,694 B2
(45) Date of Patent: May 12, 2020

(54) ACCESS SHEATH WITH INTEGRATED CLOSURE DEVICE

(71) Applicant: BOSTON SCIENTIFIC LIMITED, Hamilton (BM)

(72) Inventors: Medha Tyagi, Delhi (IN); Sumit Agrawal, Haryana (IN); Raghav Goel, New Delhi (IN); Sneha Ralli, Ghaziabad (IN); Charudatta Chandrakant Aradhye, Maharashtra (IN); Somashekar Reddy, Girgaon (IN); Ashish Chakole, Maharashtra (IN)

(73) Assignee: Boston Scientific Scimed, Inc., Maple Grove, MN (US)

(*) Notice: Subject to any disclaimer, the term of this patent is extended or adjusted under 35 U.S.C. 154(b) by 156 days.

(21) Appl. No.: 15/678,717

(22) Filed: Aug. 16, 2017

(65) Prior Publication Data

US 2018/0050176 A1    Feb. 22, 2018

Related U.S. Application Data

(60) Provisional application No. 62/375,967, filed on Aug. 17, 2016.

(51) Int. Cl.
*A61M 25/06* (2006.01)
*A61B 17/132* (2006.01)
(Continued)

(52) U.S. Cl.
CPC ....... *A61M 25/0662* (2013.01); *A61B 17/132* (2013.01); *A61B 17/1325* (2013.01);
(Continued)

(58) Field of Classification Search
CPC .......... A61M 25/02; A61M 2025/0213; A61M 2025/026; A61M 2025/028;
(Continued)

(56) References Cited

U.S. PATENT DOCUMENTS

| 5,263,943 A | 11/1993 | Vanderbrook |
| 5,968,072 A | 10/1999 | Hite et al. |

(Continued)

FOREIGN PATENT DOCUMENTS

| EP | 0655258 A1 | 5/1995 |
| EP | 2529782 A1 | 12/2012 |

(Continued)

OTHER PUBLICATIONS

International Search Report and Written Opinion dated Nov. 16, 2017 for International Application No. PCT/US2017/047153.

*Primary Examiner* — Emily L Schmidt
*Assistant Examiner* — Tiffany Legette
(74) *Attorney, Agent, or Firm* — Seager, Tufte & Wickhem LLP

(57) ABSTRACT

An access sheath assembly can include an elongate sheath for accessing an interior of an artery or vein through an access point on a patient's limb and a hub that is coupled to the elongate sheath and that includes an access port configured to provide access to an interior of the elongate sheath. The assembly includes a closure device configured to fit about the patient's limb and capable of being coupled with the hub, the closure device movable between an engaged configuration in which the closure device is coupled with the hub and thus is positioned to secure the hub relative to the patient's limb and a disengaged configuration in which the closure device is apart from the hub and extends about the patient's limb at the access point in order to provide pressure to the access point.

17 Claims, 21 Drawing Sheets

(51) Int. Cl.
*A61M 1/12* (2006.01)
*A61B 17/34* (2006.01)
*A61M 25/02* (2006.01)
*A61B 17/135* (2006.01)
*A61B 17/00* (2006.01)
*A61M 39/02* (2006.01)

(52) U.S. Cl.
CPC ......... *A61B 17/3415* (2013.01); *A61M 1/125* (2014.02); *A61B 17/0057* (2013.01); *A61B 17/135* (2013.01); *A61M 39/0247* (2013.01); *A61M 2025/0213* (2013.01); *A61M 2025/0253* (2013.01); *A61M 2039/0258* (2013.01)

(58) Field of Classification Search
CPC ........ A61M 817/132; A61M 817/1325; A61M 2025/0266; A61M 2025/0264; A61M 2025/0253
See application file for complete search history.

(56) References Cited

U.S. PATENT DOCUMENTS

| | | | |
|---|---|---|---|
| 7,927,295 | B2 | 4/2011 | Bates et al. |
| 8,353,927 | B2 | 1/2013 | Lampropoulos et al. |
| 9,089,335 | B2 | 7/2015 | Okamura |
| 9,259,212 | B2 | 2/2016 | Teeslink et al. |
| 2004/0098035 | A1 | 5/2004 | Wada et al. |
| 2007/0239092 | A1 | 10/2007 | Ross |
| 2009/0137961 | A1 | 5/2009 | Bracken |
| 2009/0281565 | A1 | 11/2009 | McNeese |
| 2011/0319830 | A1* | 12/2011 | Peters ............... A61M 25/02 604/180 |
| 2012/0046612 | A1* | 2/2012 | Scheremet ........... A61M 5/158 604/179 |
| 2012/0053617 | A1* | 3/2012 | Benz ................ A61B 17/1325 606/203 |
| 2013/0023734 | A1* | 1/2013 | Okamura ........... A61B 17/1325 600/227 |
| 2014/0031861 | A1 | 1/2014 | Teeslink et al. |

FOREIGN PATENT DOCUMENTS

| | | |
|---|---|---|
| EP | 2647359 A1 | 10/2013 |
| WO | 2014037960 A1 | 3/2014 |

\* cited by examiner

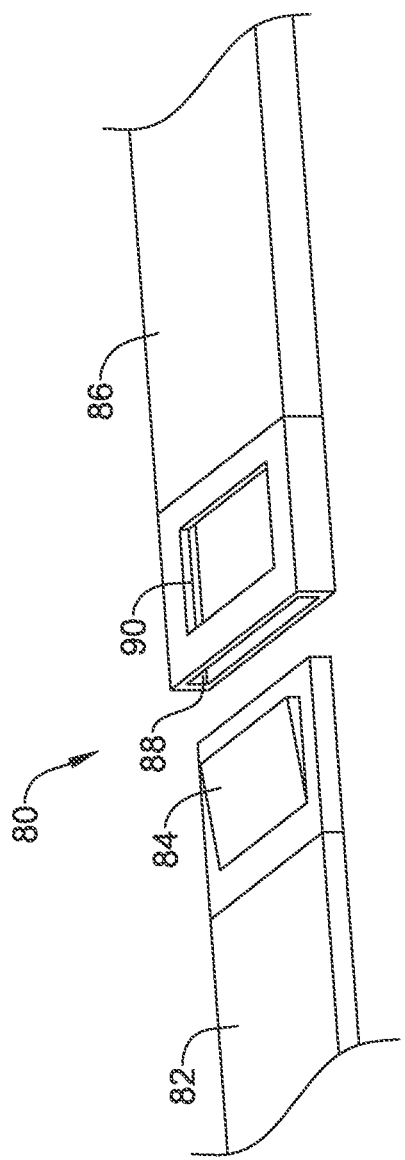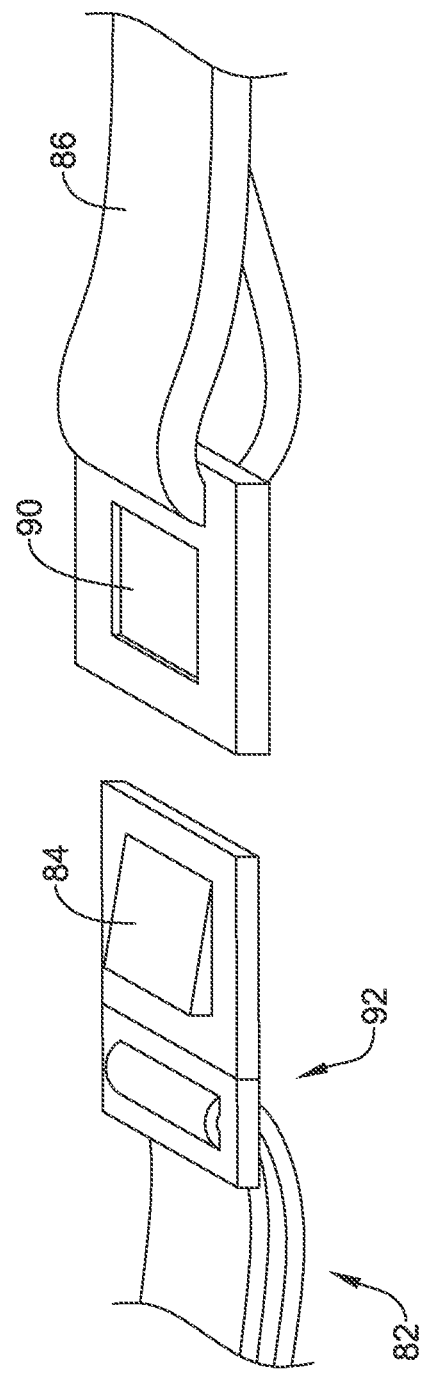

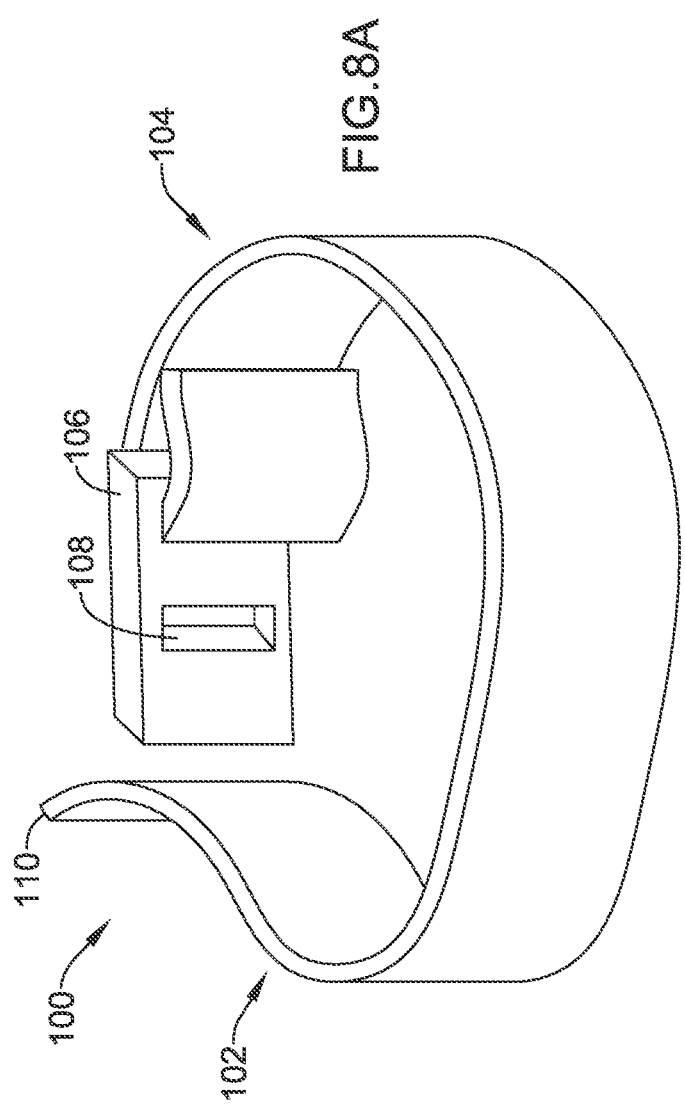
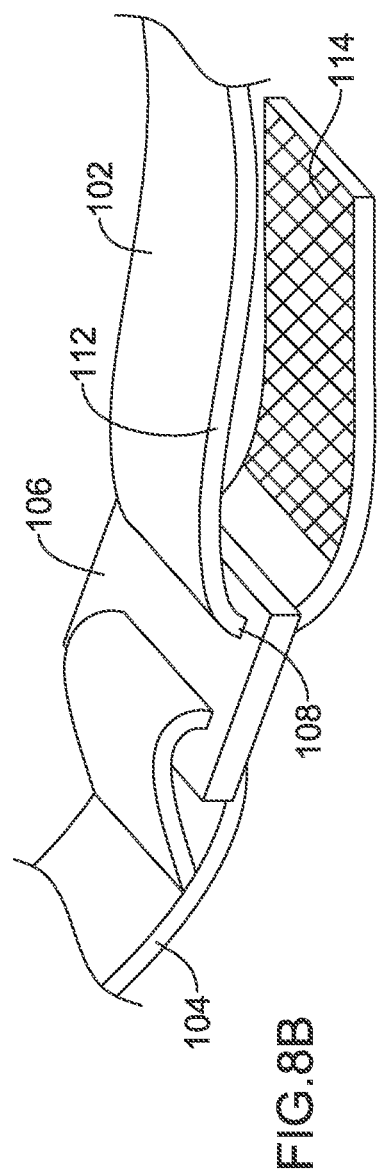
FIG.8A
FIG.8B

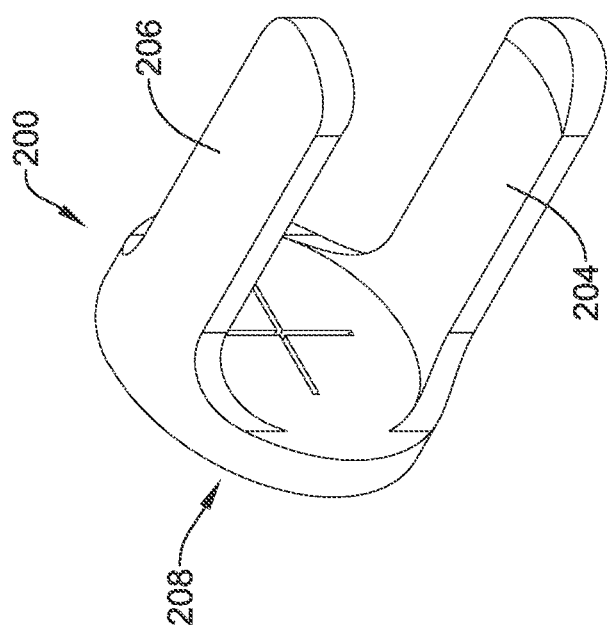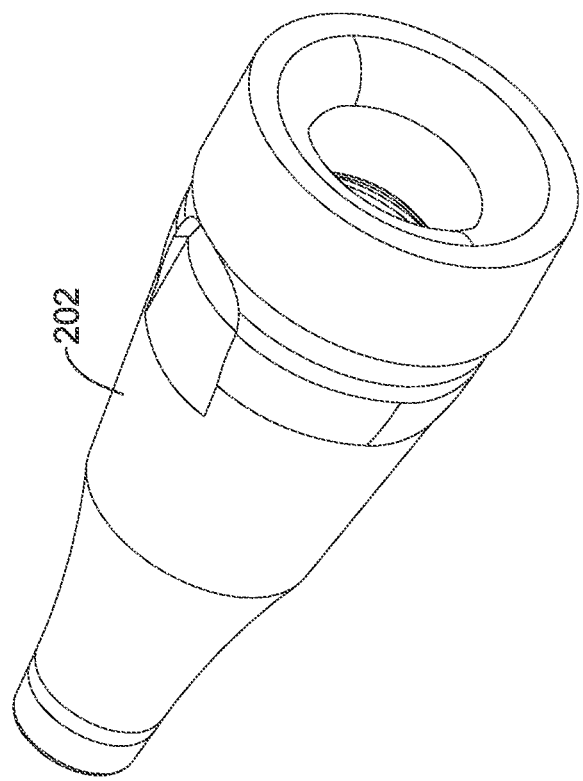
FIG. 20

ACCESS SHEATH WITH INTEGRATED CLOSURE DEVICE

CROSS REFERENCE TO RELATED APPLICATIONS

The present application claims the benefit of and priority to U.S. Provisional Patent Application Ser. No. 62/375,967, filed Aug. 17, 2016, the disclosure of which is incorporated herein by reference

TECHNICAL FIELD

The disclosure is directed to devices for accessing arteries such as the radial artery and more particularly is directed to devices for accessing the radial artery that include a closure device such as an integrated closure device.

BACKGROUND

A variety of medical procedures are performed from within a patient's vascular system, with several different access points frequently used. In some cases, access to the vascular system is gained via the femoral artery in the leg. In some cases, access to the vascular system may be gained via the radial artery or other vasculature within the patient's arm. A variety of devices may be used for gaining access via the radial artery. In some cases, a first device is used for gaining access and a second device is subsequently used to close the access point. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and uses thereof. For example, the disclosure is directed to a vascular access sheath assembly that may be used to gain access to an artery or vein as well as to subsequently help to provide pressure on the access point in order to help close the access point. In some cases, the vascular access sheath assembly includes an elongate sheath for accessing an interior of an artery or vein through an access point on a patient's limb and a hub that is coupled to the elongate sheath and that includes an access port configured to provide access to an interior of the elongate sheath. The assembly includes a closure device configured to fit about the patient's limb and capable of being coupled with the hub, the closure device movable between an engaged configuration in which the closure device is coupled with the hub and thus is positioned to secure the hub relative to the patient's limb and a disengaged configuration in which the closure device is apart from the hub and extends about the patient's limb at the access point in order to provide pressure to the access point.

Alternatively or additionally to any of the embodiments above, the closure device includes a viewing window that permits visualization of the access point when the closure device is in the disengaged configuration.

Alternatively or additionally to any of the embodiments above, the hub further includes a track and the closure device includes a complementary slot that accommodates the track and enables the closure device to slid relative to the hub.

Alternatively or additionally to any of the embodiments above, the hub further includes a track stop disposed at an end of the track opposite that of the elongate sheath that is configured to limit motion of the closure device in a direction away from the elongate sheath.

Alternatively or additionally to any of the embodiments above, the closure device includes an adjustment mechanism that extends around the patient's limb and is adjustable in diameter in order to switch between the engaged configuration and the disengaged configuration.

Alternatively or additionally to any of the embodiments above, the adjustment mechanism includes a first region having a hook section and a second region having a loop section, and the first region is adjustably securable to the second region in order to adjust a diameter of the closure device.

Alternatively or additionally to any of the embodiments above, the adjustment mechanism includes a first end including a strap and a second end including a buckle, and the strap is adjustably insertable into the buckle in order to adjust a diameter of the closure device.

Alternatively or additionally to any of the embodiments above, the adjustment mechanism includes a first region with a toothed track and a second region bearing a gear that is rotatably engageable with the toothed track in order to adjust a diameter of the closure device.

Alternatively or additionally to any of the embodiments above, the access port extends axially through the hub and the hub further comprises a fluid port extending radially through the hub.

Alternatively or additionally to any of the embodiments above, the closure device includes a bellows that is connectable to the elongate sheath, a strap portion that extends from the bellows and is configured to fit about the patient's limb, and a removable connector portion extending between the bellows and the hub.

Alternatively or additionally to any of the embodiments above, the hub includes a first hub securable to the elongate sheath, with the closure device coupled with the first hub, and a second hub insertable into the first hub, an elongate member extending from the second hub and insertable into the elongate sheath. The second hub is disposed within the first hub when the closure device is in the engaged configuration and the second hub is removed from the first hub when the closure device is in the disengaged configuration.

In another example of the disclosure, an assembly for accessing an artery via an access point on a patient's forearm is disclosed. The assembly includes a hub including an axially aligned port configured to permit insertion of an elongate member through the axially aligned port and an elongate sheath secured to and extending distally from the hub. A closure device is slidingly coupled with the hub and is movable between an engaged configuration in which the closure device is coupled with the hub and a disengaged configuration in which the closure device has been slid away from the hub. A viewing window is disposed within the closure device and is positioned to enable viewing of the access point when the closure device is in the disengaged configuration and disposed over the access point.

Alternatively or additionally to any of the embodiments above, in the engaged configuration, the closure device is configured to secure the hub and elongate sheath relative to the forearm.

Alternatively or additionally to any of the embodiments above, in the disengaged configuration, the closure device is configured to provide pressure to the access point.

Alternatively or additionally to any of the embodiments above, the closure device is configured to be able extend around the forearm when in the engaged configuration and when in the disengaged configuration.

Alternatively or additionally to any of the embodiments above, the hub further includes a track and the closure device includes a complementary slot that slidingly engages the track.

Alternatively or additionally to any of the embodiments above, the hub further includes a track stop disposed at an end of the track opposite that of the elongate radial sheath and configured to limit motion of the closure device in a direction away from the elongate radial sheath.

Alternatively or additionally to any of the embodiments above, the closure device includes an adjustment mechanism that extends around the forearm and is adjustable in diameter in order to switch between the engaged configuration and the disengaged configuration.

In another example of the disclosure, an assembly is disclosed. The assembly includes an elongate sheath for accessing an interior of a radial artery through an access point on a patient's forearm and a hub that is coupled to the elongate sheath, the hub including an access port configured to provide access to an interior of the elongate sheath. A bellows is connectable to the elongate shaft with the elongate shaft extending through the bellow, with a strap portion extending from the bellows and configured to fit about the forearm. A removable connector extends between the bellows and the hub. The radial access sheath assembly has an engaged configuration in which the removable connector is connected to the bellows and a disengaged configuration in which the removable connector is disconnected from the bellows. In the engaged configuration, the strap portion extends about the forearm and secures the hub relative to the forearm and in the disengaged configuration, the bellows can be slid off the elongate sheath and placed over the access point to provide pressure to the access point with the strap portion secured about the forearm.

Alternatively or additionally to any of the embodiments above, the strap portion is adjustable in effective size in order to switch between the engaged configuration and the disengaged configuration.

The above summary of some embodiments is not intended to describe each disclosed embodiment or every implementation of the present disclosure. The FIGS., and Description, which follow, more particularly exemplify these embodiments.

BRIEF DESCRIPTION OF THE FIGURES

The disclosure may be more completely understood in consideration of the following description of in connection with the accompanying drawings, in which:

FIG. 7A and 7B are schematic illustrations of an adjustment mechanism useable with the vascular access sheath assembly of FIG. 1;

FIG. 8A and FIG. 8B are schematic illustration of an adjustment mechanism useable with the vascular access sheath assembly of FIG. 1;

FIG. 19 and FIG. 20 are illustrations of a closure device in accordance with an embodiment of the disclosure.

Figure 1:
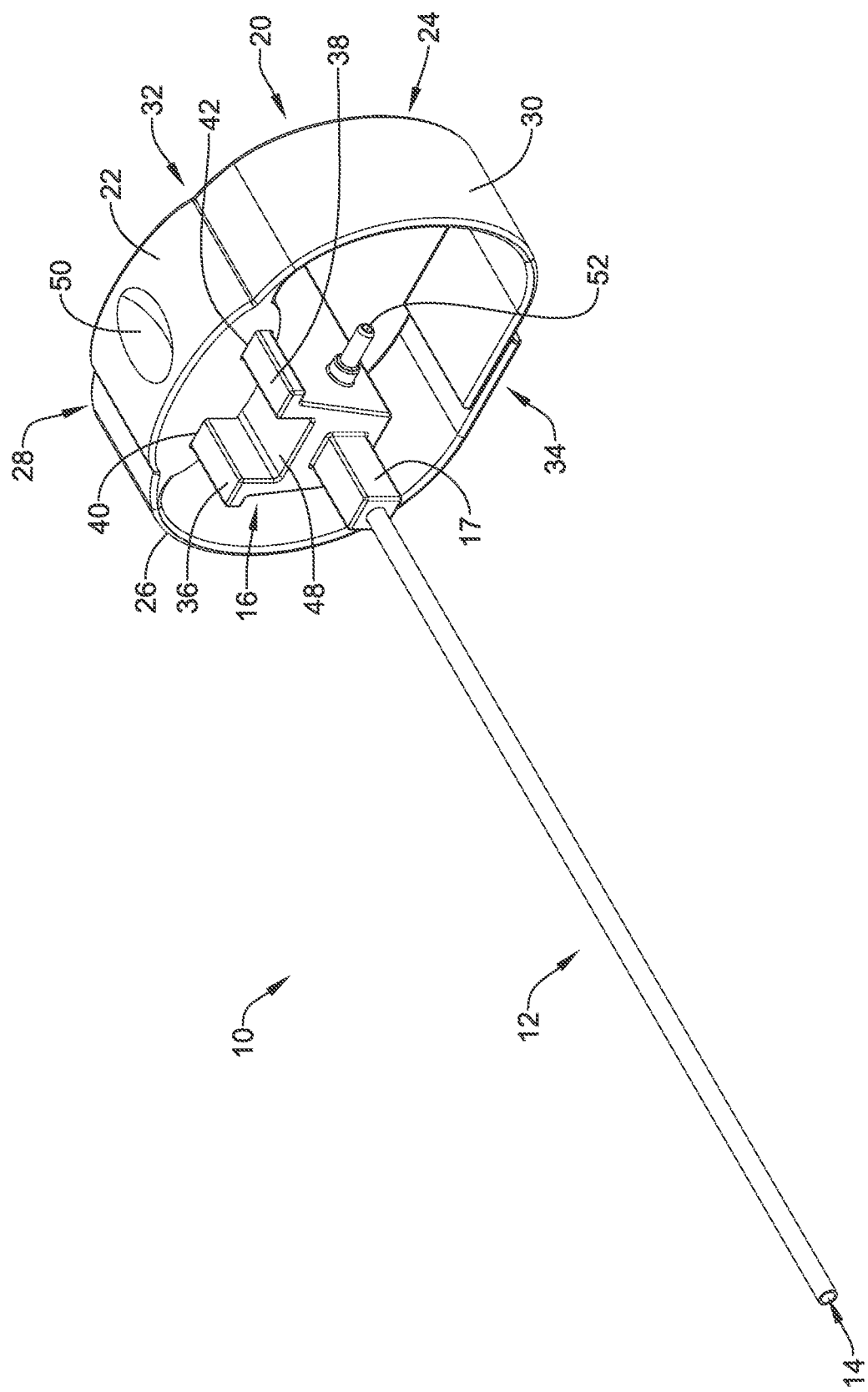
FIG. 1 is a perspective view of a vascular access sheath assembly in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 2:
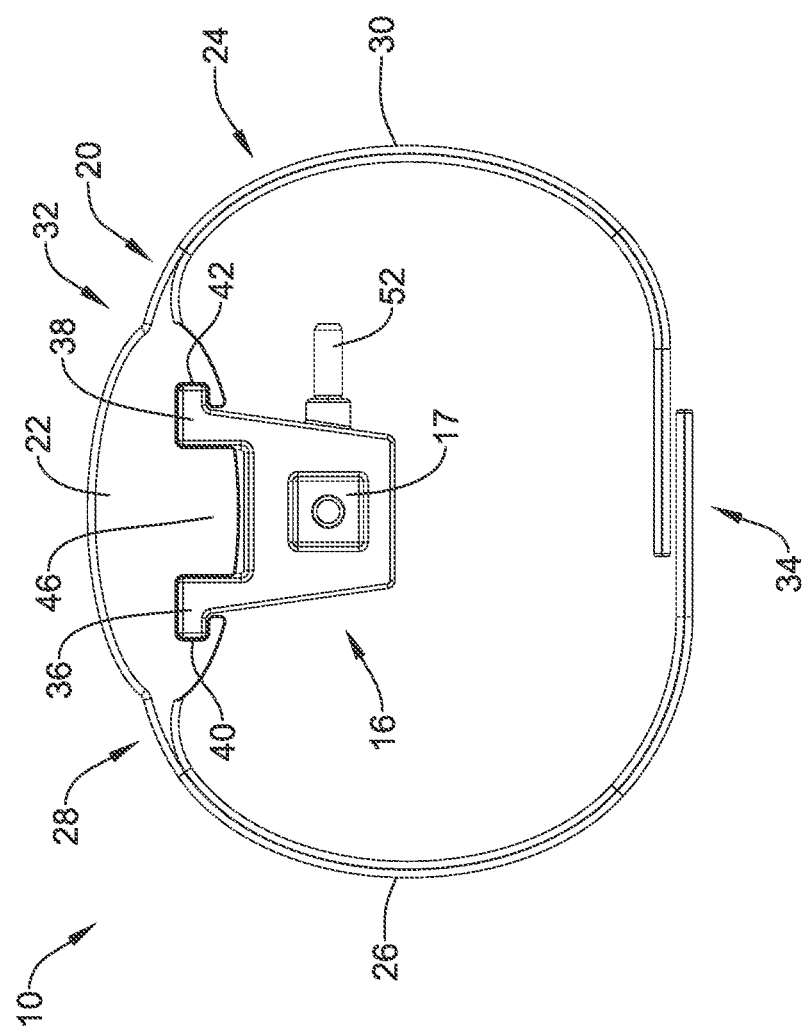
FIG. 2 is a front view of the vascular access sheath assembly of FIG. 1.
Figure 3:
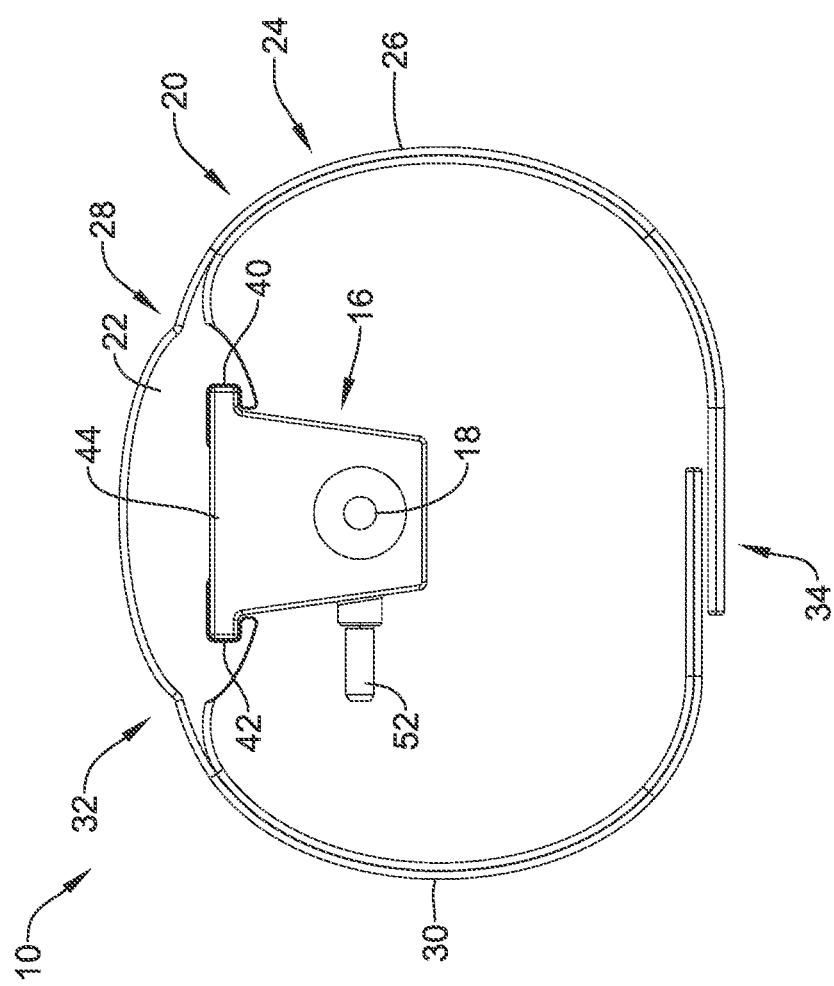
FIG. 3 is a back view of the vascular access sheath assembly of FIG. 1.

FIG. 1 is a perspective view of a vascular access sheath assembly 10 while FIG. 2 is a front view and FIG. 3 is a back view of the vascular access sheath assembly 10. The vascular access sheath assembly 10 may, for example, be used to gain access to an artery or vein within a patient's limb. In some cases, the vascular access sheath assembly 10 may be used on a patient's arm to gain access to an artery or a vein within the arm. For example, the vascular access sheath assembly 10 may be used to access a radial artery or an ulnar artery within the patient's forearm, or perhaps the brachial artery in the patient's upper arm. In some cases, the vascular access sheath assembly 10 may be used on a patient's leg to gain access to an artery or a vein within the leg, such as but not limited to, the femoral artery in the upper leg.

For ease of illustration, the vascular access sheath 10 will be described and illustrated with respect to accessing a patient's radial artery through an access point on the skin. The vascular access sheath 10 may secure itself relative to the patient during a procedure utilizing the vascular access sheath assembly 10 to gain access to the interior of the radial artery, and to help close the access point. In some cases, as illustrated, the vascular access sheath assembly 10 includes an elongate sheath 12 that may, for example, be configured to access an interior of a radial artery (or other vasculature) through an access point on a patient's forearm. The elongate sheath 12 defines a lumen 14 extending through the elongate sheath 12 that can be dimensioned to permit other elongate devices and/or members to be extended through the lumen 14 in order to reach a desired position within an initially accessed vascular structure such as the radial artery or within the vasculature beyond the initially accessed vascular structure.

The elongate sheath 12 is coupled to a hub 16. In some cases, the hub 16 includes an extension 17 that is configured to secure the elongate sheath 12 to the hub 16. In some instances, the extension 17 includes a cylindrical aperture sized to accommodate the elongate sheath 12. The elongate sheath 12 may be frictionally engaged within the extension 17. In some cases, the elongate sheath 12 may be adhesively secured to the hub 16 and/or within the extension 17. In some cases, as illustrated, the hub 16 includes an access port 18 that extends through the hub 16 and provides access to the lumen 14 extending through the elongate sheath 12. It will be appreciated that the access port 18 may be dimensioned to permit other elongate devices and/or members to be extended through the access port 18 and thus through the lumen 14 in order to reach a desired position within an initially accessed vascular structure such as the radial artery or within the vasculature beyond the initially accessed vascular structure. In some cases, while not illustrated, the hub 16 and/or the access port 18 may include structure that enables a hub of an elongate device and/or member to be temporarily secured to the hub 16.

The vascular access sheath assembly 10 includes a closure device 20 that is configured to fit about a patient's forearm (or leg, for example) and that is capable of being coupled with the hub 16. In some cases, the closure device 20 is movable between an engaged configuration and a disengaged configuration. In the engaged configuration, as shown for example in FIG. 1, the closure device 20 is coupled with the hub 16 and is positioned to secure the hub 16 relative to the forearm in order to help prevent excessive movement of the elongate sheath 12 and/or the hub 16 while the elongate sheath 12 extends into the patient's forearm. In the disengaged configuration, as will be discussed for example with respect to FIG. 12, the closure device 20 is separated from the hub 16 and is configured to extend around the forearm at an access point in order to provide pressure to the access point to reduce or eliminate bleeding from the access point.

In some instances, the closure device 20 includes a central portion 22 and an adjustable band portion 24 extending from the central portion 22. The adjustable band portion 24 may be configured to extend around a patient's forearm, for example, and may be adjustable in order to switch between the engaged configuration and the disengaged configuration. In some cases, the adjustable band portion 24 may be considered as including a first portion 26 extending from a first side 28 of the central portion 22 and a second portion 30 extending from a second side 32 of the central portion 22. In some cases, the first portion 26 overlaps or otherwise engages the second portion 30 at a securement location 34. The first portion 26 may engaged the second portion 30 in any suitable fashion, including but not limited to hook and loop fasteners (Velcro®), a belt buckle, and the like. Examples of particular fastening techniques will be discussed further with respect to subsequent drawings.

Figure 4:
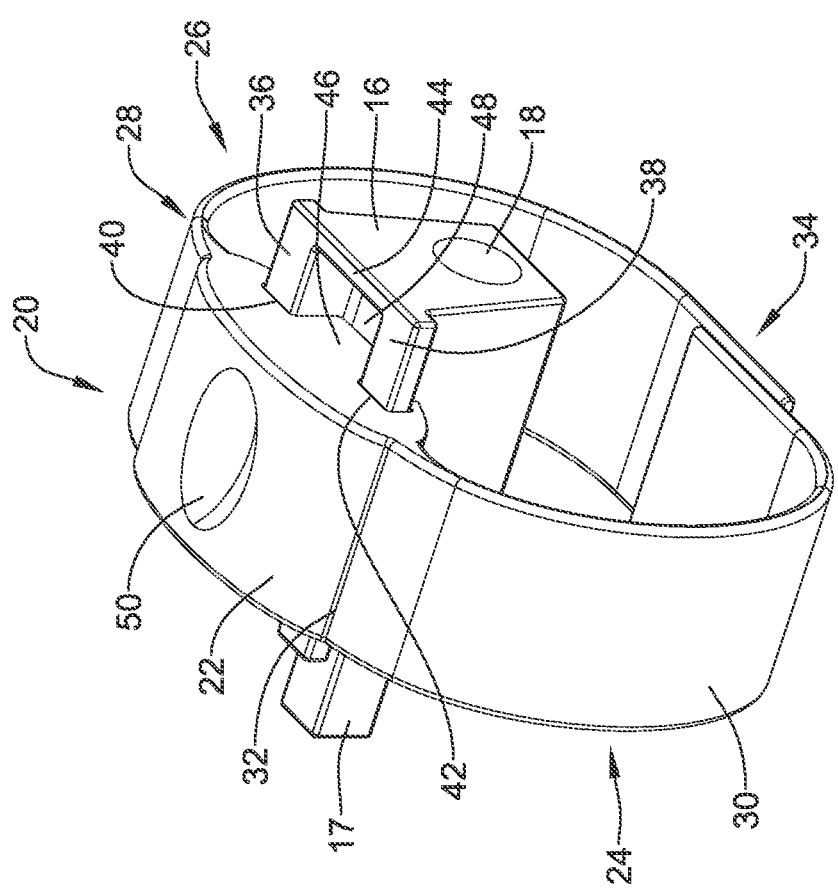
FIGS. 4 and 5 are a perspective view of the vascular access sheath assembly of FIG. 1, showing relative movement between components of the vascular access sheath assembly.
Figure 5:
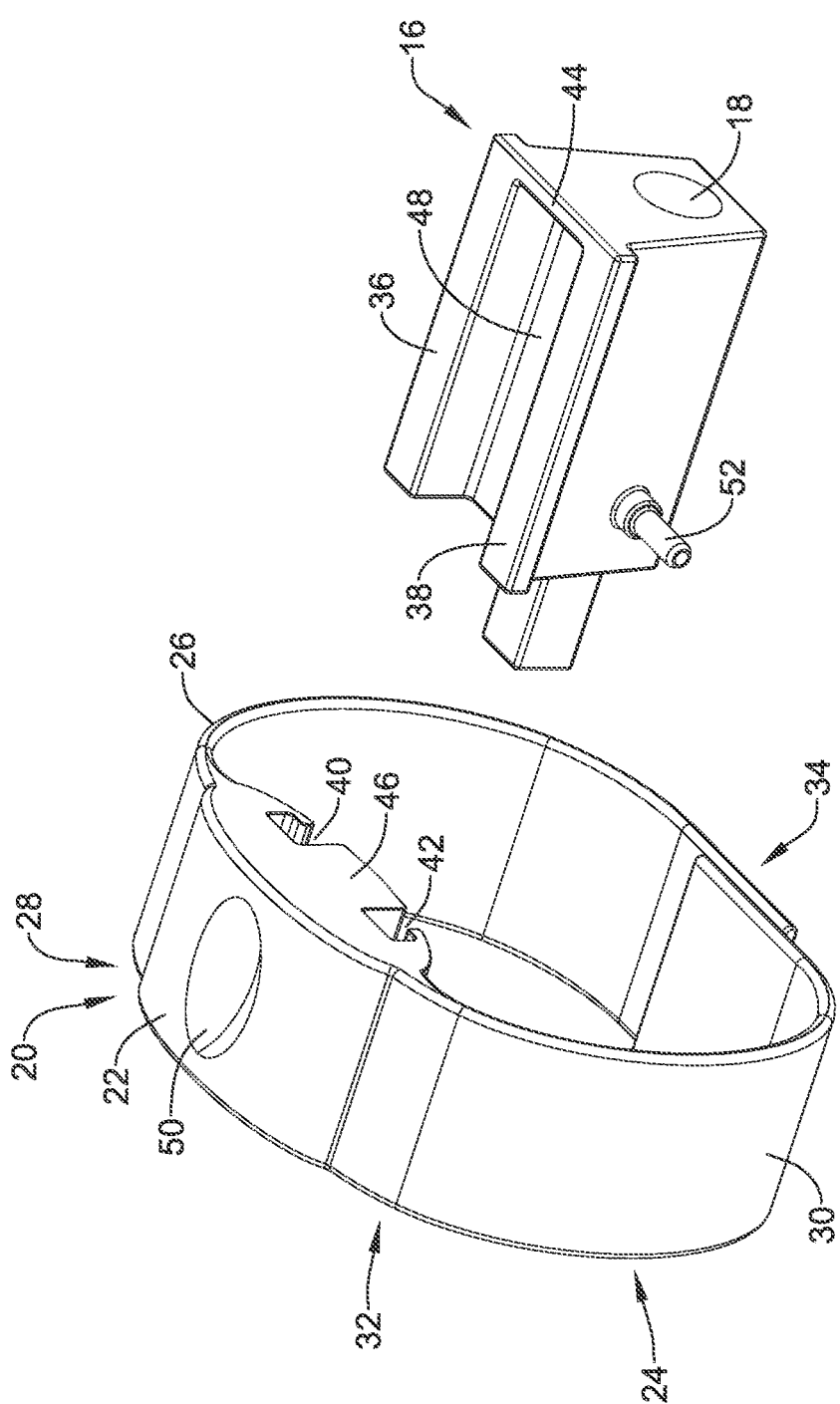

In some cases, the closure device 20 may include a slot that may be configured to slidingly accommodate a corresponding track formed within the hub 16. In some cases, as illustrated, the hub 16 includes a first track 36 and a second track 38. The closure device 20 may include a first slot 40 and a second slot 42 that accommodate the first track 36 and the second track 38, respectively. It will be appreciated that the closure device 20, therefore, is able to slide back and forth relative to the hub 16. This can be seen, for example, in FIG. 4 and FIG. 5. In FIG. 4, it can be seen that the closure device 20 has slid a short distance, relative to the hub 16, in a direction towards the elongate sheath 12. In FIG. 5, the closure device 20 has been slid a sufficient distance to remove the closure device 20 from the hub 16.

In some cases, as illustrated, the hub 16 includes a track stop 44 that interacts with the closure device 20 to limit travel of the closure device 20 in a direction opposite that of the elongate sheath 12. In some cases, the central portion 22 of the closure device 20 includes an extension region 46 disposed between the first slot 40 and the second slot 42 that fits into a void 48 formed in the hub 16, between the first track 36 and the second track 38. In some cases, a window 50 may extend through the central portion 22 of the closure device 20. In some cases, the window 50 may be formed of a transparent polymer making up part of the closure device 20. In some instances, the window 50 may simply be a void in the central portion 22 of the closure device 20. As shown, for example with respect to FIG. 12, the window 50 may permit visualization of the access point when the closure device 20 is in the disengaged configuration in order to permit one to visually detect bleeding or other potential problems with or at the access point.

In some cases, the hub 16 may include a fluid port 52. The fluid port 52 may be used for flushing out the hub 16 and/or the elongate sheath 12. The fluid port 52 may, for example, be used to inject contrast fluid for improved visualization of a particular vascular structure or other body structure under various visualization methods and techniques. In some cases, as shown, the fluid port 52 may extend radially from the hub 16 and may intersect the axially aligned access port 18.

As noted above, the first portion 26 of the adjustable band portion 24 overlaps or otherwise engages the second portion 30 of the adjustable band portion 24 at the securement location 34, and is releasably securable in a variety of manners. FIG. 6A, FIG. 6B, FIG. 7A, FIG. 7B, FIG. 8A and FIG. 8B provide illustrative but non-limiting examples of ways in which the first portion 26 may be releasably secured to the second portion 30. These securements may, for example, be incorporated into the vascular access sheath assembly 10 (FIG. 1).

Figure 6A:
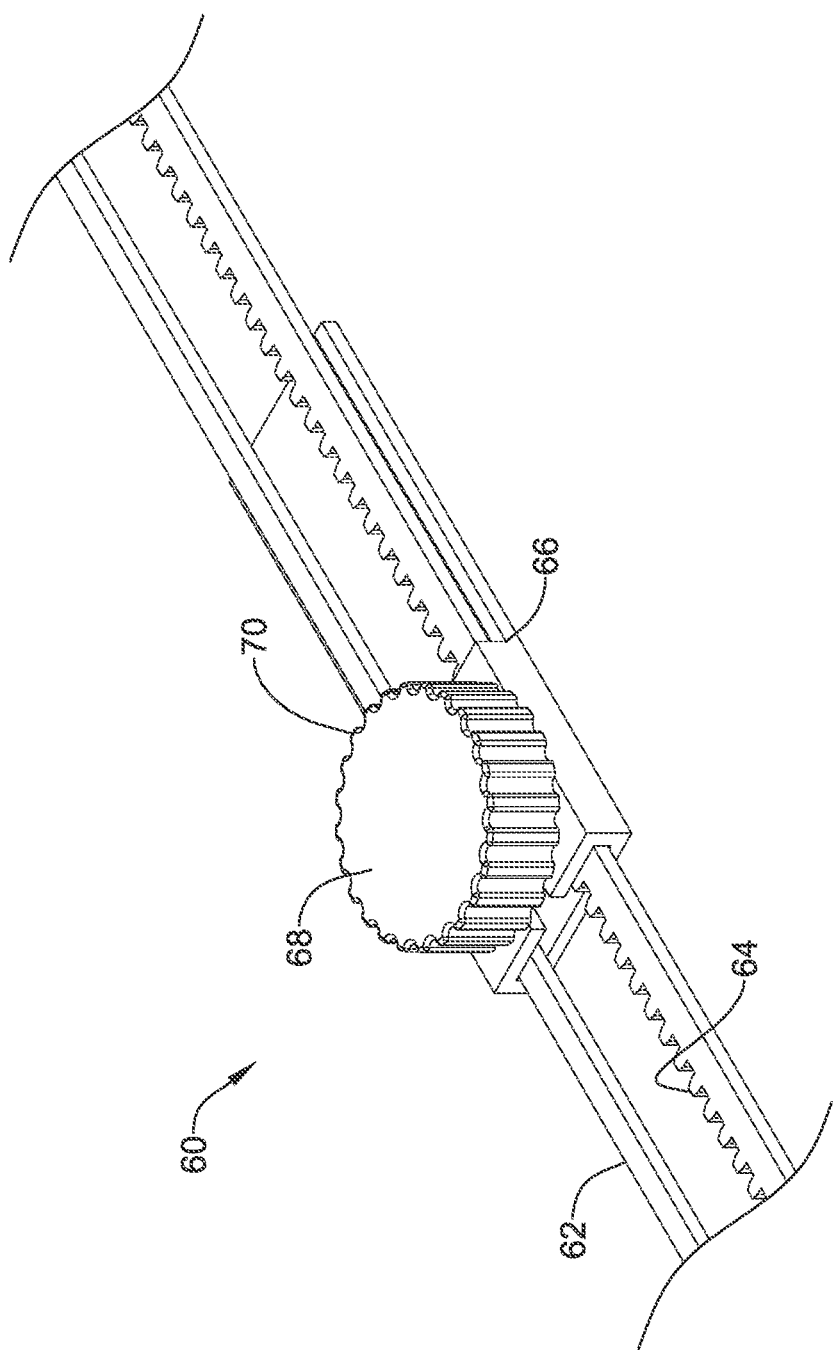
FIG. 6A is a perspective view of an adjustment mechanism useable with the vascular access sheath assembly of FIG. 1.

FIG. 6A is a perspective view of an adjustment mechanism 60 in which a first band portion 62 (which may, for example, represent the first portion 26 of the adjustable band portion 24 shown in FIG. 1 through FIG. 5) includes a toothed track 64 and a second band portion 66 (which may, for example, represent the second portion 30 of the adjustable band portion 24) includes a gear 68 that is rotatably engageable with the toothed track 64. By rotating the gear 68 in a first direction, it is possible to move the first band portion 62 relative to the second band portion 64 in a direction that effectively enlarges the size of the closure device 20 (for example). By rotating the gear 68 in a second direction, it is possible to move the first band portion 62 relative to the second band portion 64 in an opposing direction that effectively decreases the size of the closure device 20.

Figure 6B:
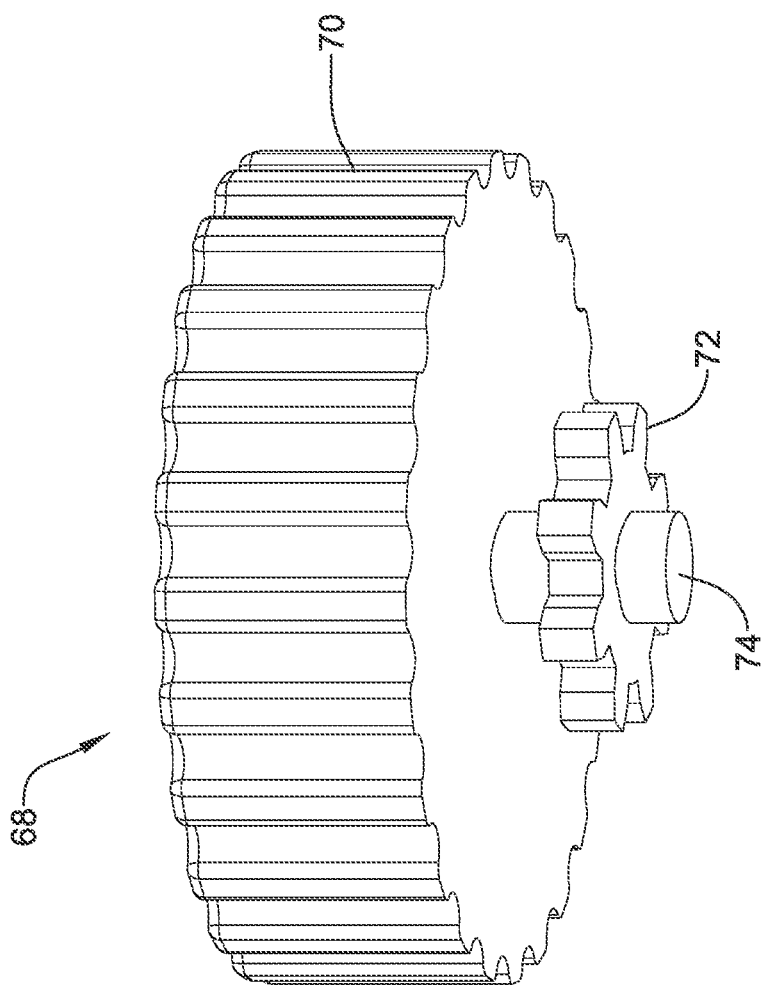
FIG. 6B is an enlarged view of a portion of the adjustment mechanism of FIG. 6A.

FIG. 6B provides an enlarged view of the gear 68. In some cases, as illustrated, the gear 68 may include an upper graspable portion 70 and a lower track engagement portion 72 that may be configured, for example, to engage the toothed track 64 and thus convert rotation of the gear 68 into relative linear motion between the first band portion 62 and the second band portion 64. In some cases, the lower track engagement portion 72 may be disposed or otherwise formed on a post 74.

FIG. 7A and FIG. 7B are schematic illustrations of an adjustment mechanism 80 in which a first band portion 82 (which may, for example, represent the first portion 26 of the adjustable band portion 24 shown in FIG. 1 through FIG. 5) includes a depressible button 84 and a second band portion 86 (which may, for example, represent the second portion 30 of the adjustable band portion 24) includes an aperture 88 into which the first band portion 82 may be inserted as well as an aperture 90 that accommodates the depressible button 84. In some cases, the depressible button 84 may be biased to an upward position, as shown in FIG. 7A, and be temporarily depressed in order to fit through the aperture 88. The depressible button 84 may then revert back to the biased upward position in which the depressible button 84 extends into the aperture 90, thereby securing the first band portion 82 to the second band portion 86. In some cases, as shown for example in FIG. 7B, the first band portion 82 may include a buckle assembly 92 that enables the first band portion 82 to be adjusted in effective length.

FIG. 8A and FIG. 8B are schematic illustrations of an adjustment mechanism 100 including a first band portion 102 (which may, for example, represent the first portion 26 of the adjustable band portion 24 shown in FIG. 1 through FIG. 5) and a second band portion 104 that in some cases includes a buckle 106. The buckle 106 includes a slot 108 that may be configured to accommodate an end 110 of the first band portion 102. Once the end 110 of the first band portion 102 is extended through the slot 108, it may be secured relative to itself. For example, and as shown in FIG. 8B, which is an enlargement, one side of the first band portion 102 may include a hook section 112 and an opposing side of the first band portion 102 may include a loop section 114. Together, the hook section 112 and the loop section 114 form a hook and loop connection, known commercially as Velcro®. It will be appreciated that which side of the first band portion 102 is the hook section 112 and which side is the loop section 114 does not particularly matter.

Figure 9:
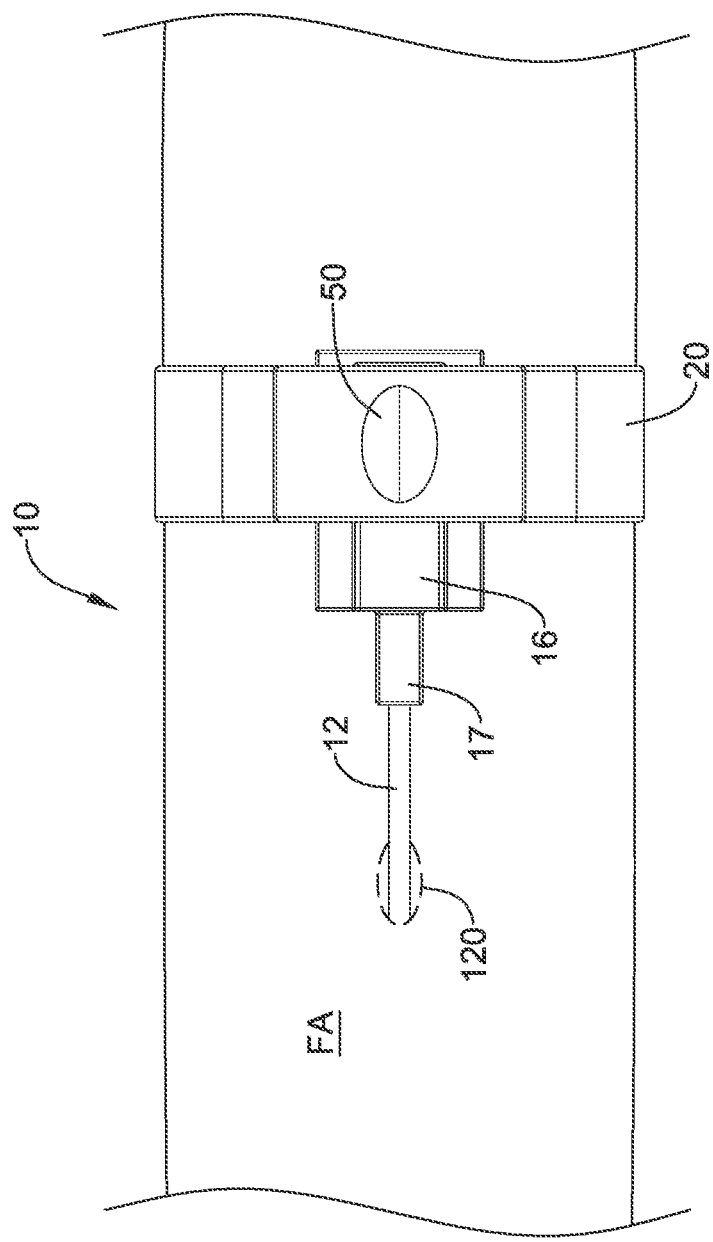
FIG. 9 through FIG. 12 illustrate use of the vascular access sheath assembly of FIG. 1.
Figure 10:
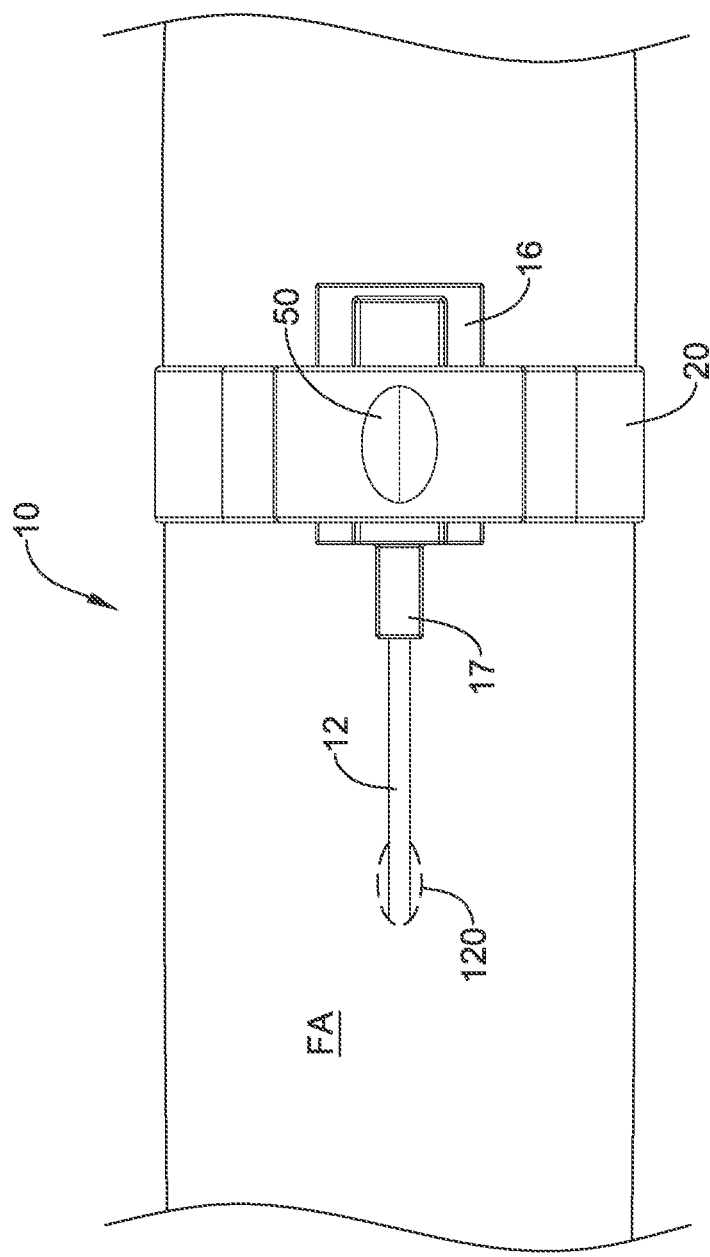
Figure 11:
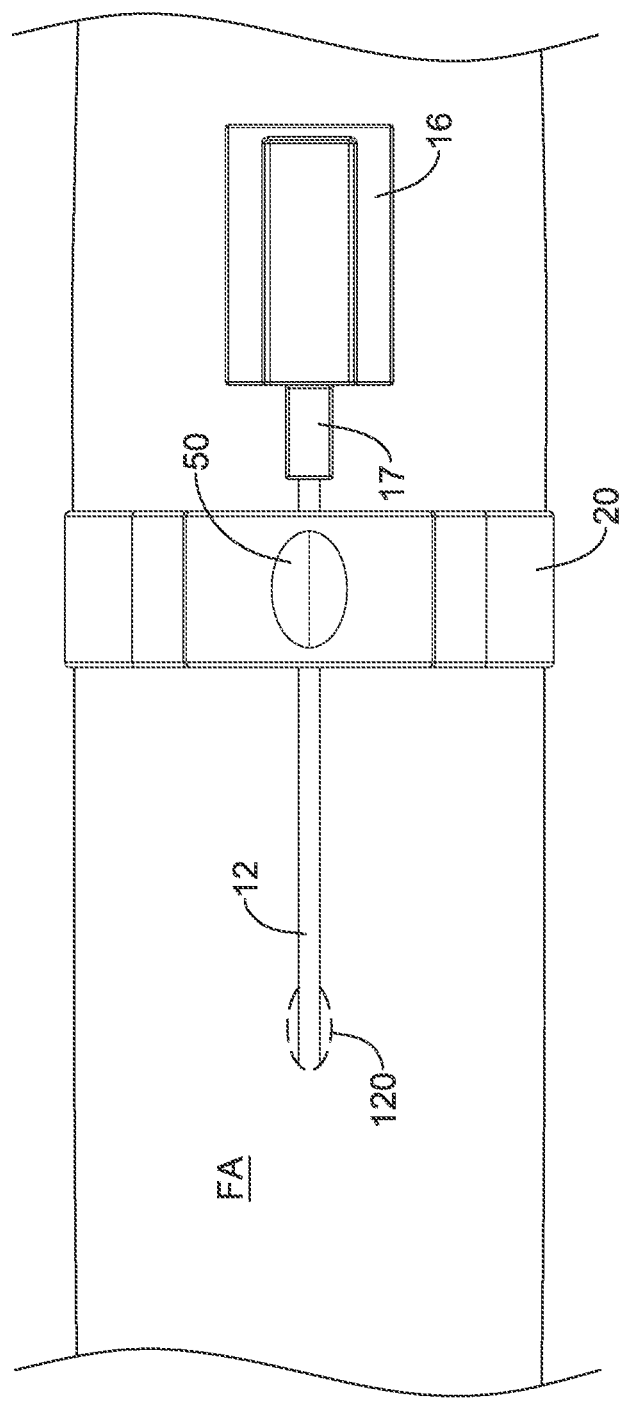
Figure 12:
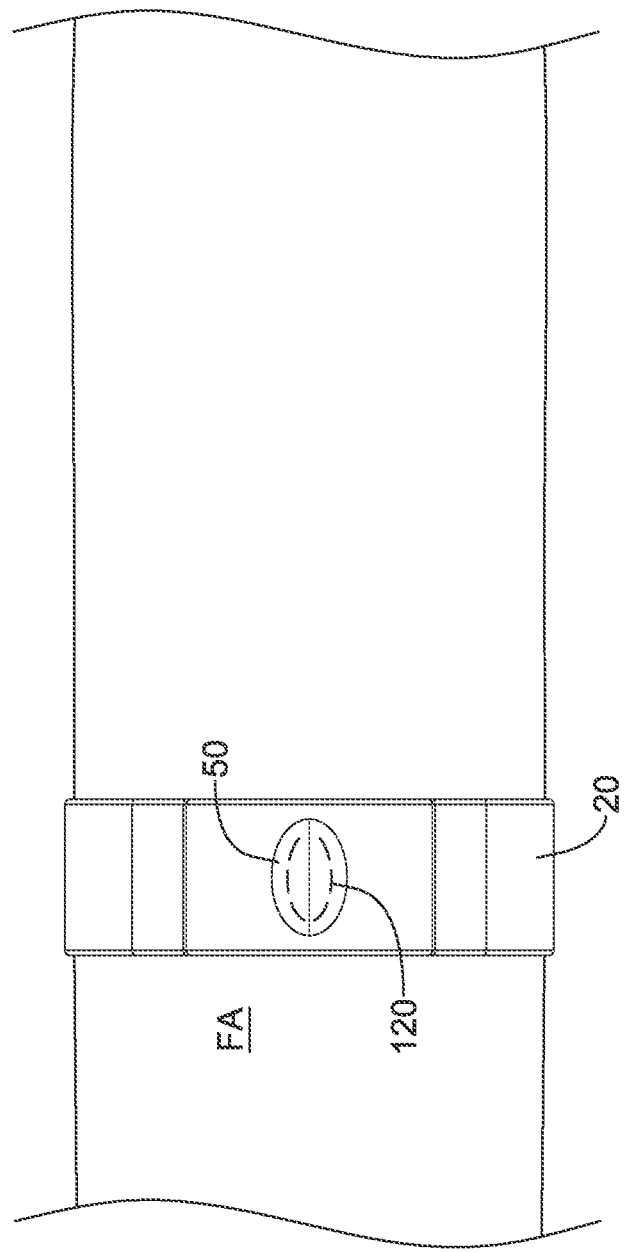

FIG. 9 through FIG. 12 provide an illustrative but non-limiting example of using the vascular access sheath assembly 10. In FIG. 9, the elongate sheath 12 may be seen as extending into the forearm FA at an access point 120. Once the elongate sheath 12 has been inserted, as shown, the closure device 20 may be secured about the forearm FA. It will be appreciated that by virtue of the closure device 20 securing the hub 16 relative to the forearm FA, this also secures the elongate sheath 12 relative to the forearm FA and thus protects against what would otherwise be a free end of the elongate sheath 12 from moving around or getting caught on other equipment. FIG. 10 represents sliding the closure device 20 towards the access point 120. FIG. 11 represents the closure device 20 having been slid far enough to be free of the hub 16. As shown in FIG. 12, the elongate sheath 12 and hub 16 have been removed from the forearm FA and the closure device 20 is positioned with the window 50 disposed over the access point 120. Once the closure device 20 has been moved into this position, the closure device 20 may be further tightened against the forearm FA in order to apply pressure to the access point 120. In some cases, the strap extending around the forearm may be adjusted in length in order to change the pressure being applied to the access point 120. It will be appreciated that the extension region 46 of the closure device 20 may be shaped or otherwise configured to help apply pressure. In some cases the extension region 46 of the closure device 20 may include additional adjustable structures such as but not limited to a rotating gear mechanism, an inflatable mechanism, a cam shaft, push buttons, and the like, for adjusting the size and shape of the extension region 46, and thus possibly adjusting the pressure applied by the extension region 46.

Figure 13:
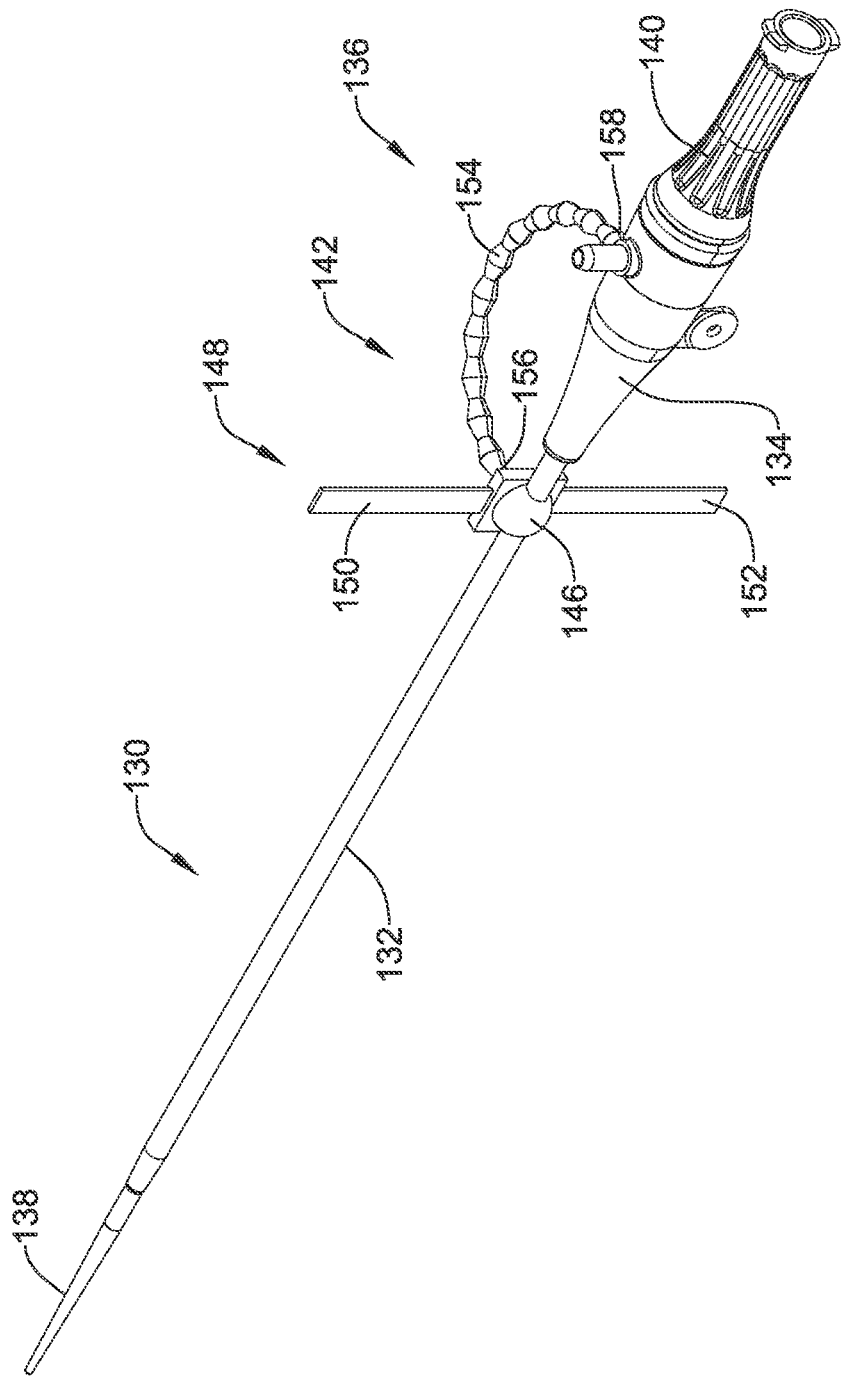
FIG. 13 and FIG. 14 are illustrations of a sheath assembly in accordance with an embodiment of the disclosure.
Figure 14:
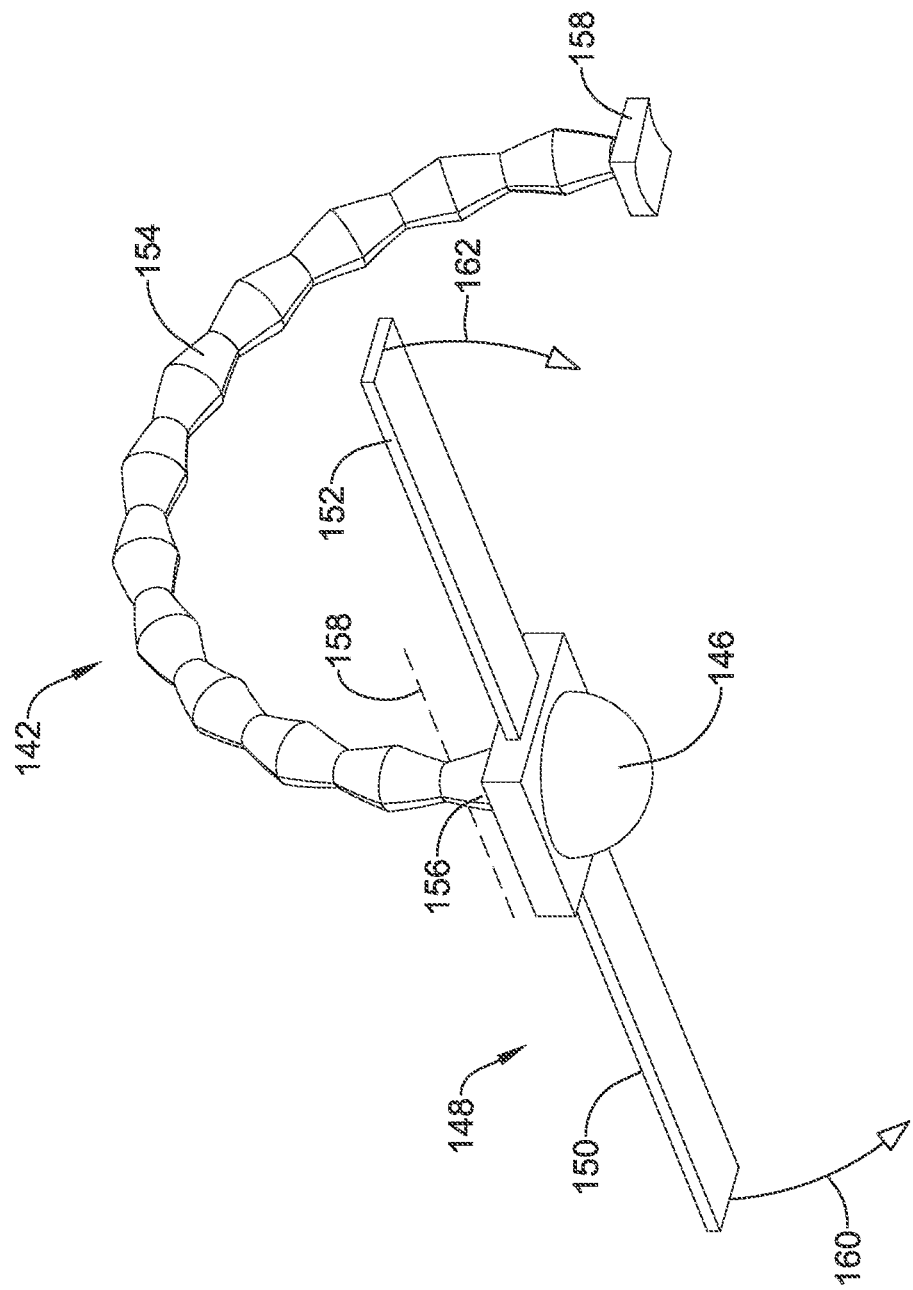
Figure 15:
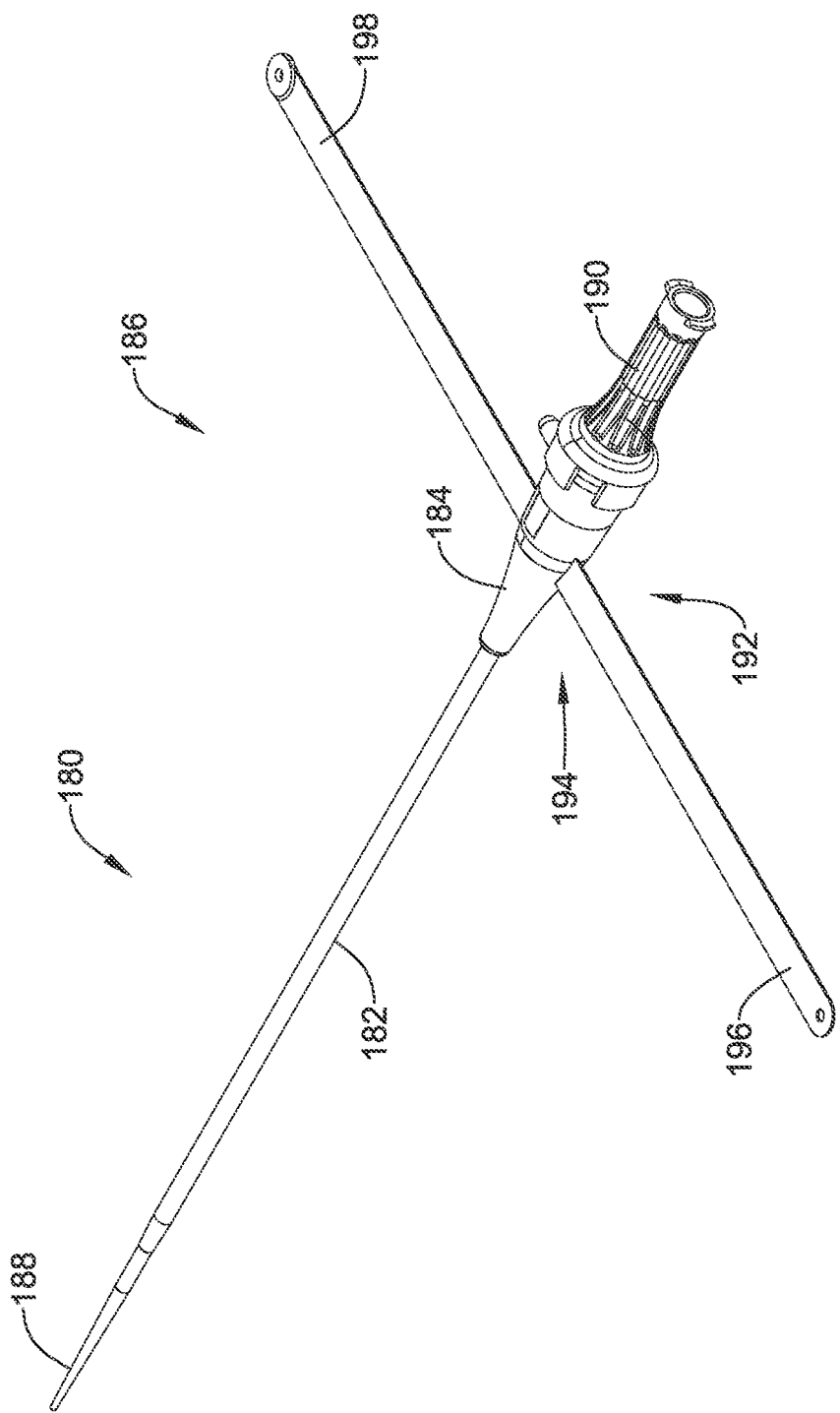
FIG. 15 through FIG. 18 are illustrations of a sheath assembly in accordance with an embodiment of the disclosure.
Figure 16:
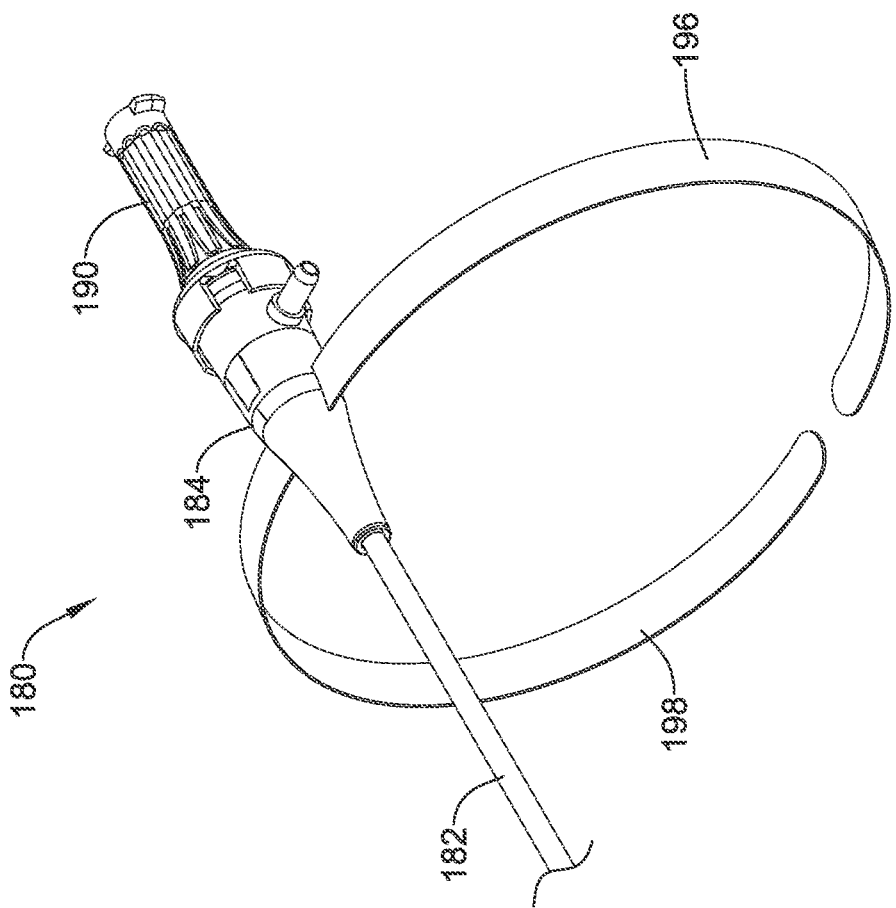

FIG. 13 and FIG. 14 provide views of a sheath assembly 130. The sheath assembly 130 includes an elongate sheath 132 that in some cases, as illustrated, may be coupled with a strain relief 134. In some cases, as shown, a dilator 136, including an elongate shaft 138 and a dilator hub 140 may extend through the strain relief 134 and the elongate sheath 132. A coupling device 142 may be used to secure the sheath assembly 130 relative to the forearm FA (FIG. 9 through FIG. 12) while the elongate sheath 132 extends into the patient and may subsequently be used to apply pressure to an access point such as the access point 120. FIG. 14 is an enlargement of the coupling device 142. The coupling device 142 generally includes a bellows 146 that is mountable on the elongate sheath 132, and/or is configured to be slidingly disposed on the elongate sheath 132. A strap portion 148 extends from the bellows 146. In some cases, the strap portion 148 may be considered as including a first strap portion 150 and a second strap portion 152. It will be appreciated that the first strap portion 150 and the second strap portion 152, in combination, may be sized to fit around the forearm FA, and to include any of the securements discussed with respect to FIG. 6A and 6B, FIG. 7A and 7B, and FIG. 8A and 8B. The coupling device 142 also includes a connector portion 154 extending from a first end 156 coupled to the bellow 144 to a second end 158 coupled to the strain relief 134.

After the procedure necessitating radial access, and as seen in FIG. 14, the connector portion 154 may be severed from the bellows 146, as seen at cut line 158. The bellows 146 may then be slid proximally off of the elongate sheath 132 and positioned over the access point (such as the access point 120). The first strap portion 150 and the second strap portion 152 may be readjusted around the forearm FA in order to secure the bellow 144 relative to the access point and to apply pressure to the access point in order to reduce or stop bleeding from the access point. The first strap portion 150 may be moved in a direction indicated by a movement arrow 160 and the second strap portion 152 may be moved in a direction indicated by a movement arrow 162 in order to secure the first strap portion 150 and the second strap portion about the forearm FA.

FIG. 15 through FIG. 18 provide views of a sheath assembly 180. The sheath assembly 180 includes an elongate sheath 182 that in some cases, as illustrated, may be coupled with a first hub 184. In some cases, the first hub 184 provides kink resistance to the sheath assembly 180. In some cases, as shown, a dilator 186, including an elongate shaft 188 and a second or dilator hub 190 may extend through the first hub 184 and the elongate sheath 182.

A coupling device 192 may be used to secure the sheath assembly 180 relative to the forearm FA (FIG. 9 through FIG. 12) while the elongate sheath 182 extends into the patient and may subsequently be used to apply pressure to an access point such as the access point 120. The coupling device 192 includes a strap portion 194. In some cases, the strap portion 194 may be considered as including a first strap portion 196 and a second strap portion 198. It will be appreciated that the first strap portion 196 and the second strap portion 198, in combination, may be sized to fit around the forearm FA, and to include any of the securements discussed with respect to FIGS. 6A and 6B, FIGS. 7A and 7B, and FIGS. 8A and 8B.

Figure 17:
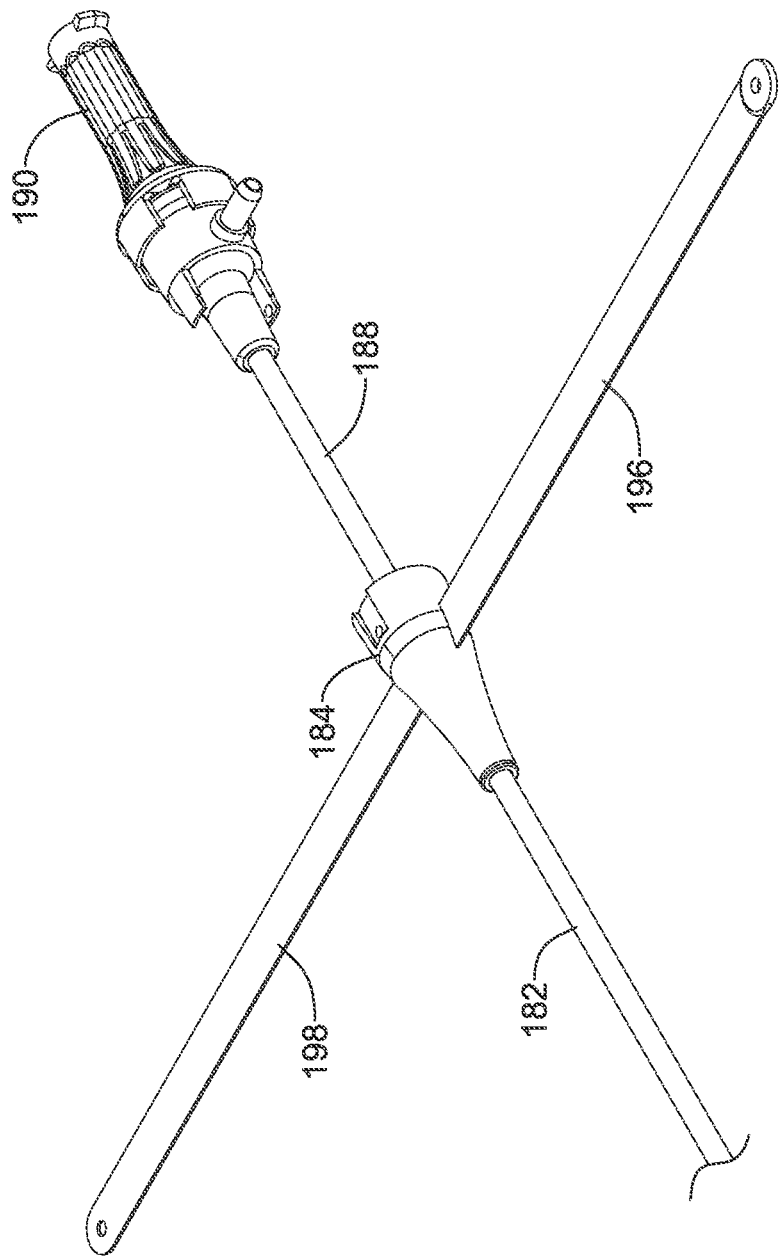
Figure 18:
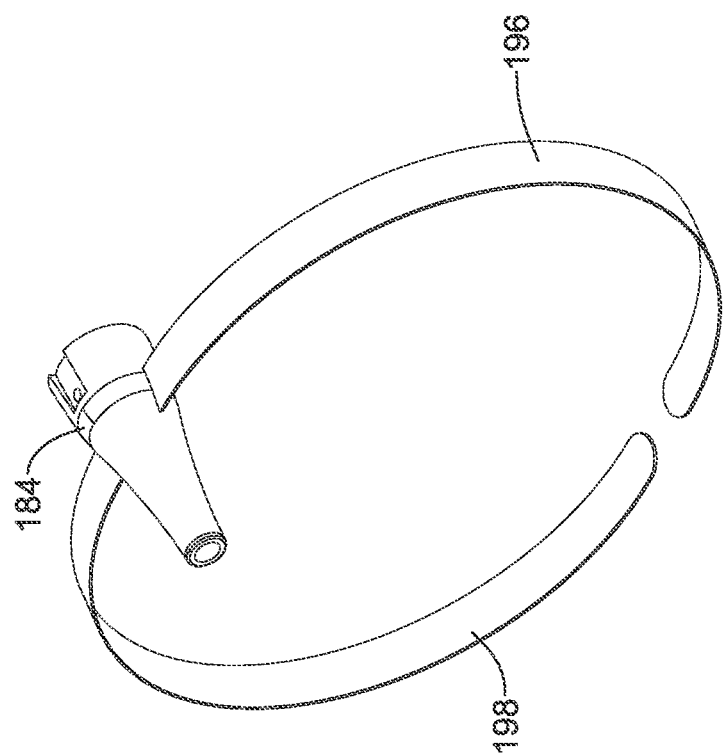

It will be appreciated that during a trans-radial artery procedure, the first strap portion 196 and the second strap portion 198 may be wrapped around the forearm FA in order to secure the strain relief 184 relative to the forearm. This configuration is illustrated, for example in FIG. 16. After the procedure, the dilator 186 may be withdrawn from the elongate sheath 182, as shown in FIG. 17. Once the strain relief 184 has been removed from the elongate sheath 182, the strain relief 184, in combination with the strap portion 194 may serve as a closure device to help apply pressure to an access point (such as the access point 120). This configuration is illustrated in FIG. 18.

Figure 19:
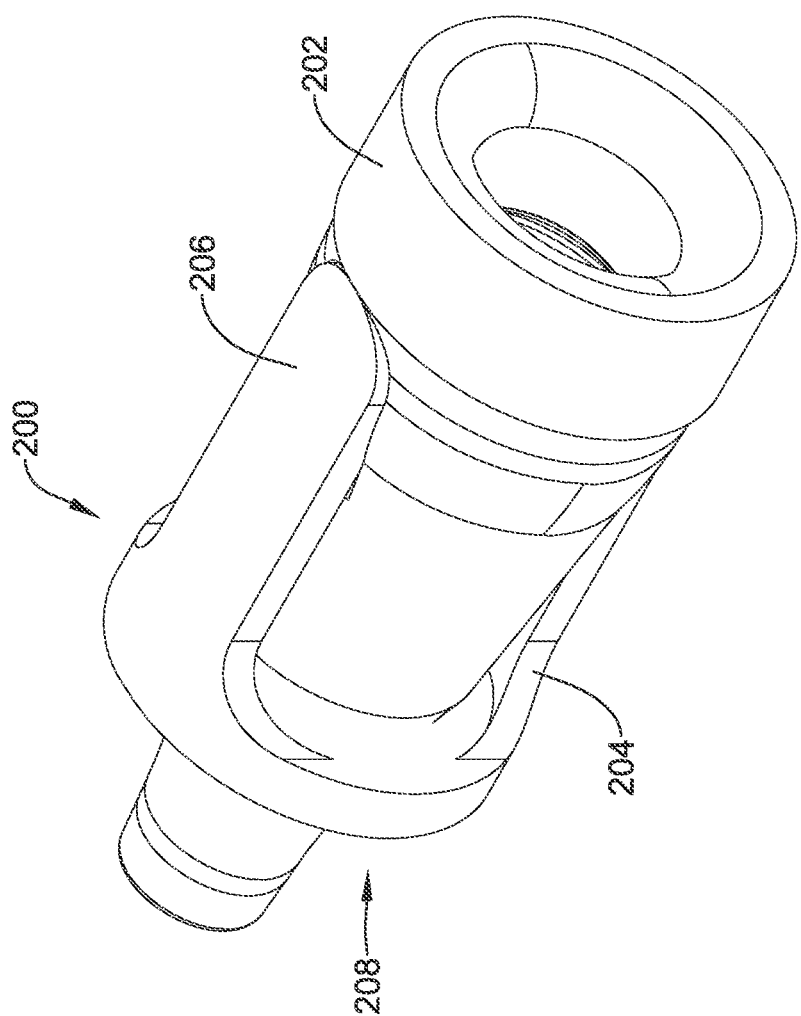

FIG. 19 and FIG. 20 are illustrations of a closure device 200 shown disposed on a strain relief 202. It will be appreciated that the strain relief 202 may generally represent a strain relief or hub that may be coupled to an elongate sheath forming part of a radial access sheath assembly. In some cases, the closure device 200 may remain on the strain relief 202, as shown in FIG. 19, until it is time to provide pressure to an access point. The closure device 200 may be formed of a compliant polymer such as silicone, and may include a first wing 204 and a second wing 206, each extending from a central portion 208. In some cases, the first wing 204 and the second wing 206 may be flattened out, and may function as adhesive bandages. In some cases, a pressure bid may be disposed proximate the central portion 208 before the closure device 200 is applied to the skin. By varying the size of the bid, it may be possible to adjust and control the relative pressure applied by the closure device 200.

It will be appreciated that a variety of different materials may be used in forming the devices described herein. In some embodiments, for example, the devices may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

The devices described herein may be formed of any suitable desired material, such as a biocompatible material including biostable, bioabsorbable, biodegradable or bioerodible materials, including in some cases one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A vascular access sheath assembly comprising: an elongate sheath adapted to access an interior of an artery or vein within a patient's limb through an access point; a hub coupled to the elongate sheath, the hub including an access port configured to provide access to an interior of the elongate sheath and a closure device configured to fit about the patient's limb and capable of being coupled with the huh, the closure device movable between an engaged configuration in which the closure device is coupled with the hub and positioned to secure the hub relative to the patient's limb at a first position proximal of the access point with the elongate sheath extending distally from the hub and the closure device to the access point and a disengaged configuration in which the closure device is apart from the hub and extends about the patient's limb at a second position distal of the first position and disposed over the access point in order to provide pressure to the access point.

2. The vascular access sheath assembly of claim 1, wherein the closure device comprises a viewing window that permits visualization of the access point when the closure device is in the disengaged configuration.

3. The vascular access sheath assembly of claim 1, wherein the access port extends axially through the hub and the hub further comprises a fluid port extending radially through the hub.

4. The vascular access sheath assembly of claim 1, wherein the closure device comprises:
   a bellows that is connectable to the elongate sheath;
   a strap portion extending from the bellows and configured to fit about the patient's limb; and
   a removable connector portion extending between the bellows and the hub.

5. The vascular access sheath assembly of claim 1, wherein the hub comprises:
   a first hub securable to the elongate sheath, with the closure device coupled with the first hub; and
   a second hub insertable into the first hub, an elongate member extending from the second hub and insertable into the elongate sheath;
   wherein the second hub is disposed within the first hub when the closure device is in the engaged configuration and the second hub is removed from the first hub when the closure device is in the disengaged configuration.

6. The vascular access sheath assembly of claim 1, wherein the hub further comprises a track and the closure device comprises a complementary slot that accommodates the track and enables the closure device to slide relative to the hub.

7. The vascular access sheath assembly of claim 6, wherein the hub further comprises a track stop disposed at an end of the track opposite that of the elongate sheath, the track stop configured to limit motion of the closure device in a direction away from the elongate sheath.

8. The vascular access sheath assembly of claim 1, wherein the closure device comprises an adjustment mechanism that is configured to extend around the patient's limb and is adjustable in diameter in order to switch between the engaged configuration and the disengaged configuration.

9. The vascular access sheath assembly of claim 8, wherein the adjustment mechanism comprises a first region having a hook section and a second region having a loop section, and the first region is adjustably securable to the second region in order to adjust a diameter of the closure device.

10. The vascular access sheath assembly of claim 8, wherein the adjustment mechanism comprises a first end including a strap and a second end including a buckle, and the strap is adjustably insertable into the buckle in order to adjust a diameter of the closure device.

11. The vascular access sheath assembly of claim 8, wherein the adjustment mechanism comprises a first region with a toothed track and a second region bearing a gear that is rotatably engageable with the toothed track in order to adjust a diameter of the closure device.

12. An assembly adapted to access an artery via an access point on a patient's forearm, the assembly comprising: a hub including an axially aligned port configured to permit insertion of an elongate member through the axially aligned port; an elongate sheath secured to and extending distally from the hub in an engaged configuration; a closure device slidingly coupled with the hub and movable between the engaged configuration in which the closure device is coupled with the hub and positioned to secure the hub relative to the patient's forearm at a first position proximal of the access point with the elongate sheath extending distally from the hub and the closure device to the access point; and a disengaged configuration in which the closure device has been slid away from the hub and extends about the patient's forearm at a second position distal of the first position, wherein the closure device is configured to be able to extend around the forearm when in the engaged configuration and when in the disengaged configuration; and a viewing window disposed within the closure device and positioned to enable viewing of the access point when the closure device, is in the disengaged configuration and disposed over the access point.

13. The assembly of claim 12, wherein in the engaged configuration, the closure device is configured to secure the hub and elongate sheath relative to the forearm.

14. The assembly of claim 12, wherein in the disengaged configuration, the closure device is configured to provide pressure to the access point.

15. The assembly of claim 12, wherein the closure device comprises an adjustment mechanism that is configured to extend around the forearm and is adjustable in diameter in order to switch between the engaged configuration and the disengaged configuration.

16. The assembly of claim 12, wherein the hub further comprises a track and the closure device comprises a complementary slot that slidingly engages the track.

17. The assembly of claim 16, wherein the hub further comprises a track stop disposed at an end of the track opposite that of the elongate sheath and configured to limit motion of the closure device in a direction away from the elongate sheath.

* * * * *